United States Patent
Wright

[19]

[11] Patent Number: 5,967,317
[45] Date of Patent: Oct. 19, 1999

[54] SYRINGE ORIENTING DISPOSABLE CONTAINER

[76] Inventor: Alan Wright, 229 Calle Serena, San Clemente, Calif. 92672

[21] Appl. No.: 09/129,695

[22] Filed: Aug. 5, 1998

[51] Int. Cl.⁶ .................................................... B65D 83/10
[52] U.S. Cl. ........................................... 206/366; 206/370
[58] Field of Search ................................... 206/364, 365, 206/366, 370; 220/229, 908

[56] References Cited

U.S. PATENT DOCUMENTS

| | | |
|---|---|---|
| 4,779,728 | 10/1988 | Hanifl et al. . |
| 4,826,073 | 5/1989 | Bruno . |
| 4,955,477 | 9/1990 | Bruno . |
| 5,076,429 | 12/1991 | Patrick et al. . |
| 5,154,345 | 10/1992 | Shillington . |
| 5,240,108 | 8/1993 | Tonna . |
| 5,387,735 | 2/1995 | Ponsi et al. . |
| 5,413,243 | 5/1995 | Bemis et al. . |
| 5,423,450 | 6/1995 | Shillington et al. . |
| 5,740,909 | 4/1998 | Nazare et al. . |

*Primary Examiner*—David T. Fidei
*Attorney, Agent, or Firm*—Gene Scott-Patent Law & Venture Group

[57] ABSTRACT

A box like container has a length dimension larger then its width dimension so as to provide an interior space capable of storing hypodermic syringes which are placed into the container, where there is insufficient space for the syringes to reverse their orientations in the container once they are placed therein. The container provides a syringe entrance having opposing flexible members so as to accept a syringe that is forcefully pushed through it and into he container, but which will not allow a syringe to back out of the container.

6 Claims, 3 Drawing Sheets

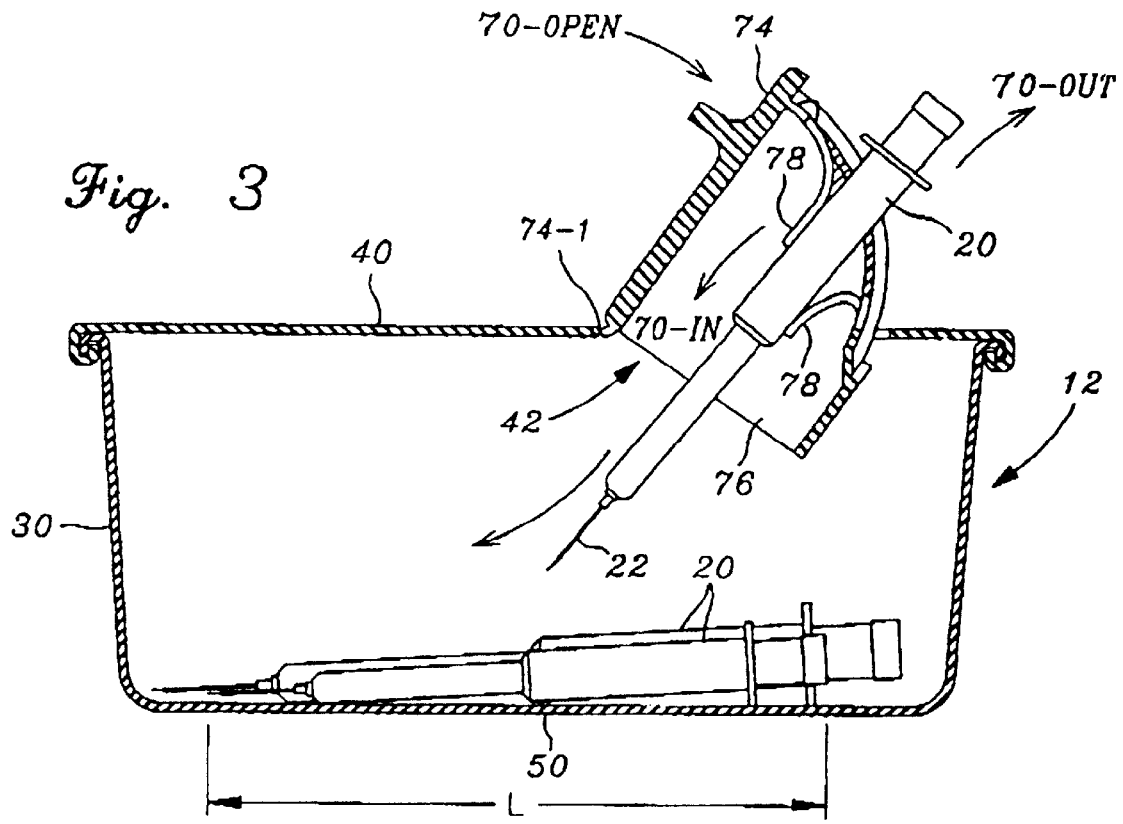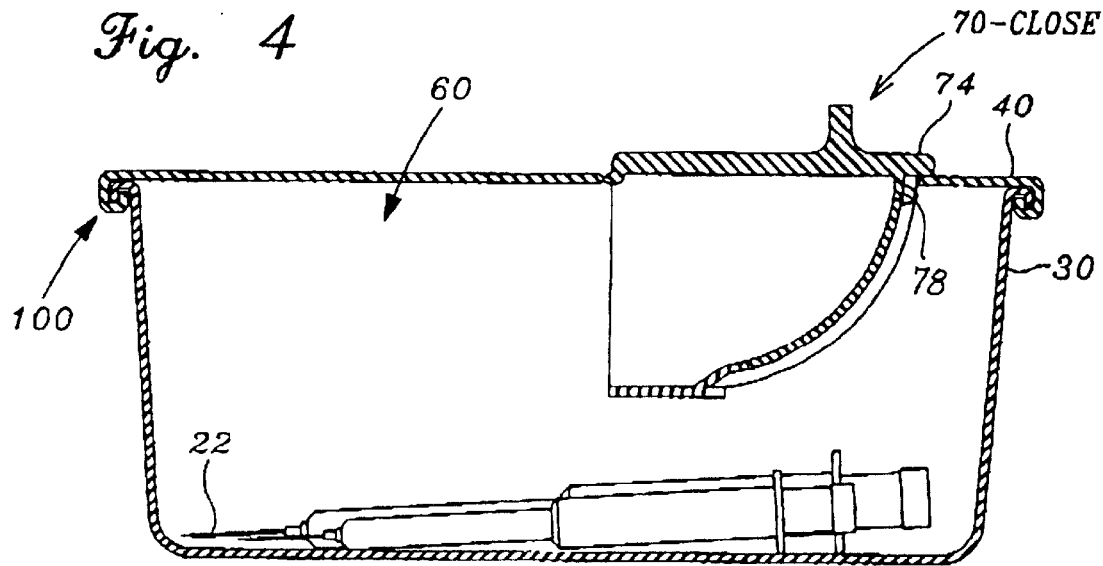

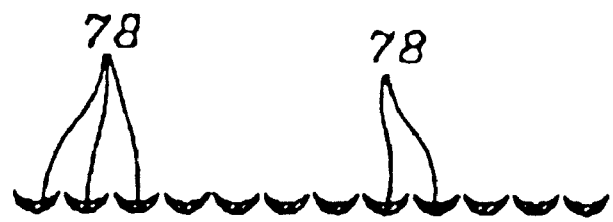
*Fig.* 6
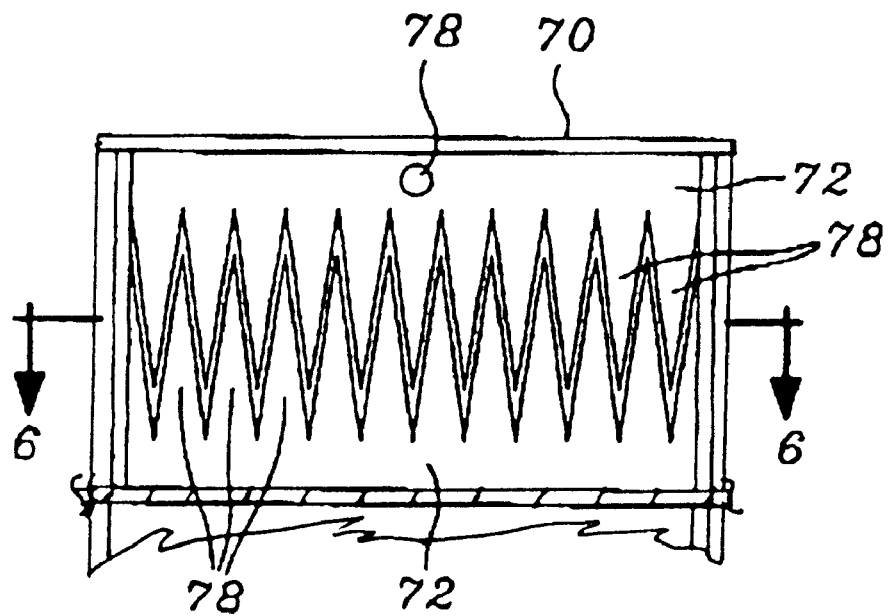
*Fig.* 5

SYRINGE ORIENTING DISPOSABLE CONTAINER

BACKGROUND OF THE INVENTION

1. Field of the Invention

This invention relates generally to storage or disposal containers for implements such as hypodermic needles, scalpel blades and related devices which come into contact with human or animal body fluids, and more particularly to such a container providing certain advantages in size, shape and entry portal type.

2. Description of Related Art

The following art defines the present state of this field:

Bemis, U.S. Pat. No. 5,413,243 describes a sharps container apparatus comprising a container including a door manually movable between a closed position and an open position, and a rubber band for binding the door toward the closed position, the container being completely closed when the door is in the closed position, a bracket adapted to be securely mounted on the wall, and inter-engaging projections and slots on the bracket and on the container for securing the container to the bracket.

Shillington, U.S. Pat. No. 5,423,450 describes a secure disposable container and mounting bracket which comprises a generally box-like enclosed container having a top shell with a limited access opening with a closure for receiving medical sharps and inhibiting human hand access, the container having a back wall with a downwardly extending slot at an upper edge, and a latching tab at a lower edge thereof, a rectangular panel having a back surface and holes for mounting it to a vertical surface, and mounting tabs for mounting the panel to another mounting bracket mounted on a vertical supporting surface, an upper edge for receiving the downwardly extending slot on the container and lever operated finger for engaging an opening in the tab on the lower edge of the container and engagement with a transverse ledge.

Shillington, U.S. Pat. No. 5,154,345 describes a secure container assembly for medical sharps and waste which comprises the combination of a substantially rigid box-like lower housing defined by upstanding front, back, and side walls terminating with a top having an upwardly extending rectangular opening for providing access to the housing, and a semi-cylindrical top curving about a generally horizontal axis secured along one edge of said top by a hinge and secured along the other edge by locking tabs for permanent securement thereto, an engagement horizontally extending access opening in said top for receiving a disposable syringe or the like, and a pivotable closure for said opening pivotally mounted about said axis within the top and having a receptacle area normally exposed to said access opening in a first position for receiving a disposed article and a curved surface for covering the access opening upon pivoting from said first position to a second position for dumping the article into said housing.

Ponsi, U.S. Pat. No. 5,387,735 describes a disposable container and a disposable system employing the disposable container. The container comprises a hollow container body having an opening at the top to permit access to the interior of the container body and having a barrier disposed adjacent the opening for restricting access to the interior of the container body. The barrier at least in part comprises a first cowl extending over the opening and a complimentary second cowl being offset relative to the first. The container includes a retention for preventing items from being dispensed through the opening from the interior of the container body when the container body is upright. The outer enclosure is shaped to accommodate the inner container, and includes a hood conforming to the first cowl.

Bruno, U.S. Pat. No. 4,955,477 describes a receptacle for storage and disposal of potentially injurious implements, which is adapted to receive implements in a compact side-by-side horizontal configuration for maximum storage capacity. Such receptacle substantially prevents implements stored therein from falling out after closure of the receptacle container which can be conveniently discarded in an appropriate disposal facility. In addition, the receptacle also prevents a person's hand from contacting such implements within the receptacle.

Nazare, U.S. Pat. No. 5,740,909 describes a sharps container which has a receptacle, cover, and tray and provides an improved locking mechanism to resist unauthorized tampering, as well as hermetically sealed construction to prevent any leakage of fluids from the container. The rotating tray provides an escapement mechanism for hands-free disposal of sharps through biasing the offset balanced tray into an open, receiving position to receive new items and deposit them into the interior of the container, and then returning to a nearly closed position. A locking mechanism is also provided to rotate the tray into a locking position thereby permanently closing the container and displacing the locking mechanism into the container interior so that the top surface of the locking mechanism is flush with the adjacent exterior container surface.

Tonna, U.S. Pat. No. 5,240,108 describes a sharps disposal system which includes a fiberboard container mounted to a wall by a lockable cage. The container has an entrance opening formed through the top, sized for the deposit of sharps into its interior. A baffle extends within the interior from the back downwardly and forwardly and is sized and positioned to discourage manual access to the interior while directing sharps into the interior. The container also includes a lid hinged to the top for movement between stable opened and closed positions to permit one hand operation when opened. For disposal the lid is secured to the top using a foam adhesive strip to provide a secure, substantially leak-proof seal. The container is coated on the inside surface with a hydrophobic material and has the seams and corners sealed to make the interior of the container substantially leakproof. A view port can be provided to determine when the container is full. Handles extend from the top to aid lifting the container from the wire cage and help prevent inadvertent sticks in the unlikely event that a needle or other sharp object has pierced the container.

Patrick, U.S. Pat. No. 5,076,429 describes a sharps container comprising a receptacle and a lid engaging the receptacle, the lid including a rotatable tray and a baffle flap for sealing the receptacle when the tray is in an open position by the force of gravity, and one or more detents may be provided to hold the tray selectively in a closed or partially closed position.

Habifl, U.S. Pat. No. 4,779,728 describes a disposal container particularly adapted for hospital use and comprising a hollow container body having a slot a the top to permit access to the interior of the container body and having a barrier disposed adjacent the spot for restricting access to the interior of the container body. The barrier comprises a first cowl extending over the slot and a complementary second cowl extending beneath the slot, and a raised shelf at one side of the slot opposite the location of the first cowl. A pivotal closure is provided for sealing of the container when filled.

The prior art teaches a variety of sharps containers including those designed particularly for hypodermic syringes. However, the prior art does not teach a used syringe container combination capable of admitting these devices yet thwarting removal in the same way as the instant invention and of particular size as to prevent rotation of the syringes within the container. The present invention fulfills these needs and provides further related advantages as described in the following summary.

SUMMARY OF THE INVENTION

The present invention teaches certain benefits in construction and use which give rise to the objectives described below.

The present invention provides a box like container having a length dimension larger then its width dimension so as to provide an interior space capable of storing hypodermic syringes which are placed into the container in a preferred orientation, because there is insufficient space for the syringes to reverse their orientations in the container once they are placed therein. The container provides a syringe entrance having opposing flexible teeth so as to accept a syringe that is forcefully pushed through the teeth and into he container, but which will not allow a syringe to move out of the container.

A primary objective of the present invention is to provide a safety disposable container for used syringes having advantages not taught by the prior art.

Another objective is to provide such a container whereby syringes may be placed into the container but not easily withdrawn from it.

A further objective is to provide such a container whereby syringes, once placed into the container cannot move about within the container so as to reverse their positions within the container, i.e. needle pointing toward the entrance, so as to present a health hazard to those using the container.

A further objective is to provide such a container having inexpensive construction so as to be economically discarded after being filled.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings:

FIG. 3 is a sectional elevational view taken along line 3—3 in FIG. 1;

FIG. 4 is a sectional elevational view taken along line 4—4 in FIG. 2;

FIG. 5 is an elevational view of the entranceway shown in FIG. 1; and

FIG. 6 is a sectional view taken along line 6—6 in FIG. 5 showing the nature of a curvature of the teeth of the entranceway.

DETAILED DESCRIPTION OF THE INVENTION

Figure 1:
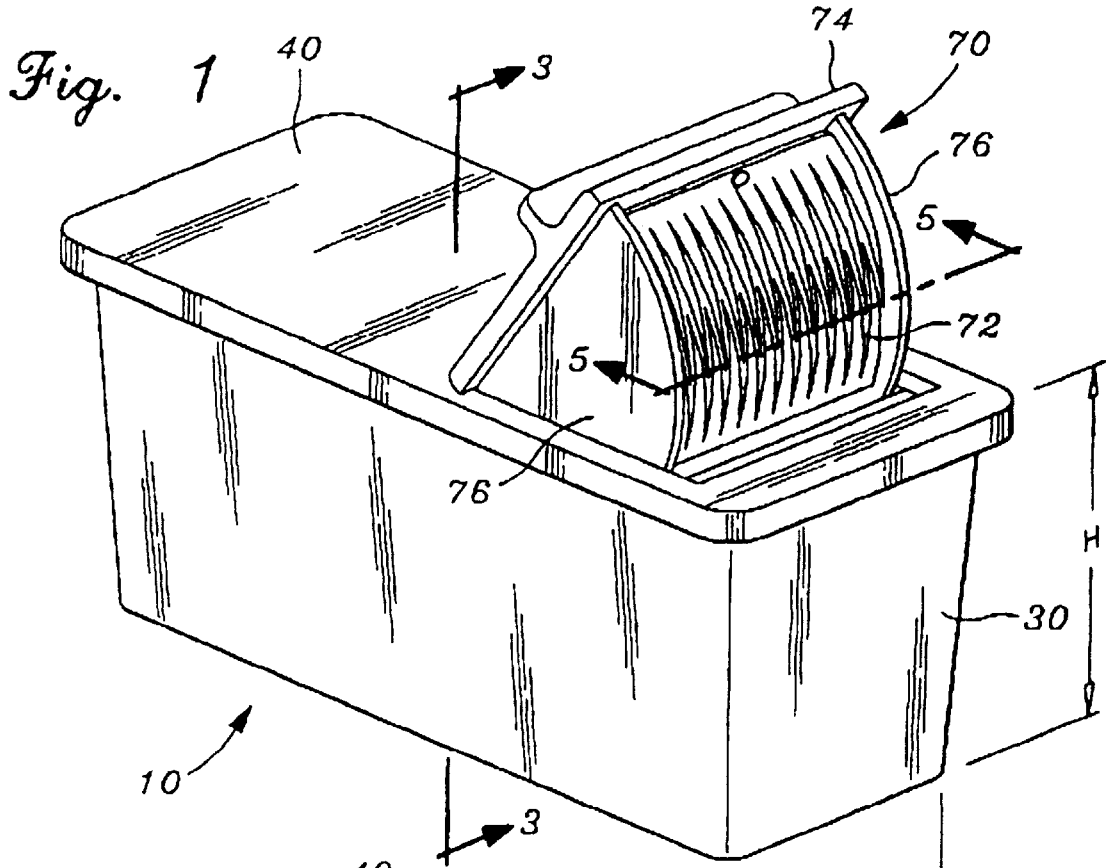
FIG. 1 is a perspective view of the preferred embodiment of the present invention showing an entrance feature in a raised position.
Figure 2:
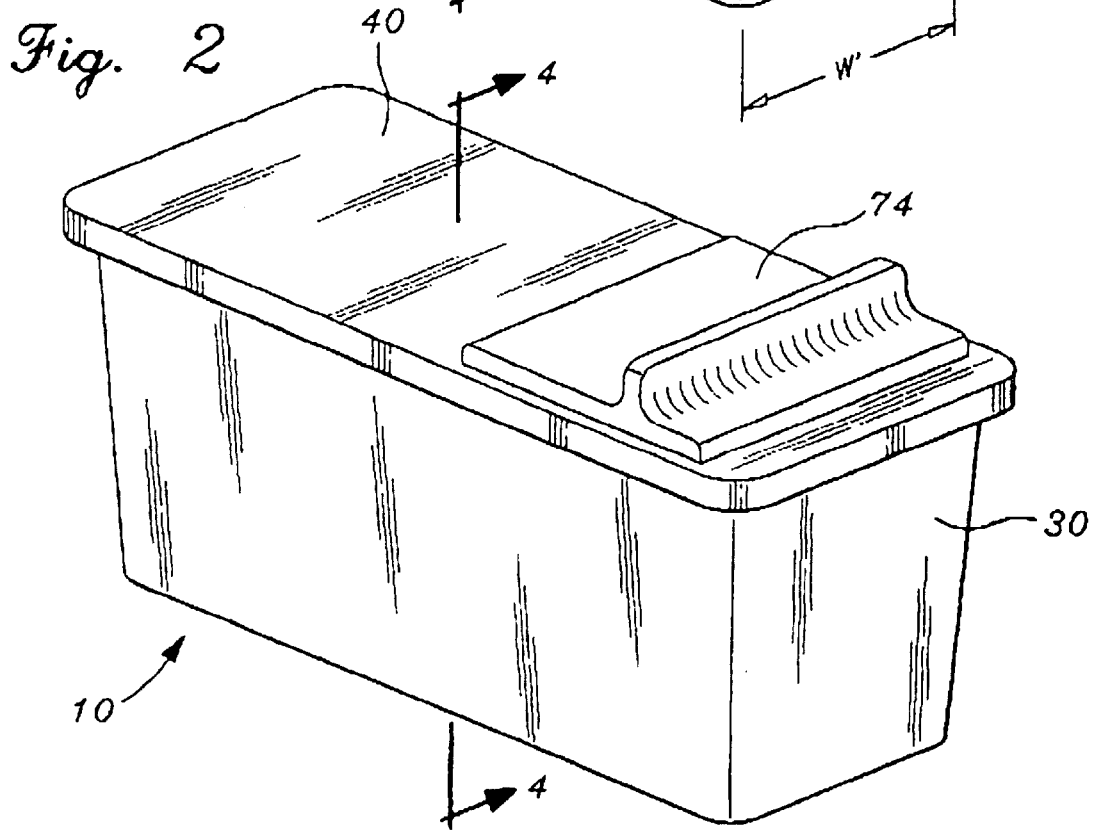
FIG. 2 is a perspective view thereof showing the entrance feature in a lowered and closed position.

The above described drawing figures illustrate the invention, a combination disposable container 10 and one or more hypodermic syringes 20 contained therein, the combination comprising the container 10 having a sidewall 30, a top cover 40 and a bottom wall 50 as shown in FIG. 1, said sidewall, top cover and bottom wall being joined so as to fully enclose an interior space 60 within the container 10. Alternately, the container 10 may be constructed as a cylinder or other shape. The container 10 provides an entranceway 70 into the interior space 60. As shown, this entranceway 70 provides for safe placement of the syringes 20 into the container 10. The plurality of hypodermic syringes 20, are each of a size as to be positionable within the entranceway 70 as shown in FIG. 3, and to be moveable through the entranceway 70 into the interior space 60 by manual pushing, so as to be captured within the container 10, i.e., falling to the bottom of the container 10, the interior space 60 being of such volume as to accept the plurality of hypodermic syringes 20 therein and of such size as to prevent each one of the hypodermic syringes 20 from being positionally reversed within the container, i.e., turned around. Preferably, the sidewall 30, top cover 40 and bottom wall 50 are of such material and construction as to inhibit penetration by a syringe needle 22. A tough plastic such as Lexan® may be used or, alternately, a thick wall of any one of the common structural plastics.

Preferably, the entranceway 70 provides a flexible element 72 movable in a first direction 70-In for admitting a one of the syringes 20 into the interior space 60, as best seen in FIG. 3, and resistant to motion in an alternate direction 70-Out so as to prevent a one of the syringes 20 from moving out of the interior space 60 through the entranceway 70.

Preferably, each of the syringes 20 has a length dimension L (FIG. 3) greater than the width W (FIG. 1) of the interior space 60 and greater then the height H of the interior space 60. Therefore, when the syringe 20 is pushed into the container, as in FIG. 3, it falls to the bottom of the container and cannot reorient itself so as to enable the needle 22 to point toward the entranceway 70.

Preferably, the entranceway 70 is mounted in the top cover 40 of the container 10 adjacent to one end 12 of the container 10 as shown in FIG. 4.

Preferably, the entranceway 70 comprises a lid flap 74 hinged integrally with the top cover 40, preferably by a living hinge 74-1, for covering an aperture 42 therein, in the present example, a square hole in the cover 40, a pair of spaced apart entranceway side walls 76 depending from the lid flap 74 and the flexible element 72 extending between the lid flap 74 and the pair of spaced apart entranceway side walls 76, the lid flap 74 being positionable between a closed position 70-Close for covering the aperture 42, the pair of spaced apart entranceway side walls 76 and the flexible element 72 extending into the interior space 60; and an open or raised position 70-Open wherein the spaced apart entranceway side walls 76, the flexible element 72 and the lid flap 74, together, fully cover the aperture 42, access to the interior space 60 being gained by pushing through the flexible element 72.

Preferably, the flexible element 70 comprises a pair of opposing and intermeshed teeth portions made of a flexible and resilient plastic sheet stock, a material having, also, some stiffness to it. Preferably, each of the intermeshed teeth portions provides a plurality of teeth 78 (FIG. 5), each formed with a lateral curvature (FIG. 6), such that each of the teeth 78 is more easily bent toward the interior space 70-In, as when a syringe is pushed through the teeth portions, than away from the interior space 70-Out.

In use the invention is preferably made with the sidewall 30 and the bottom wall 50 molded as a single piece and sealed around the upper rim 100 of the side wall to the top cover as shown in FIG. 4. The living hinge 74-1, or alternately, a plastic welded hinge is preferably biased to maintain the lid flap 74 in the closed position as shown in FIG. 4. In this position the syringes cannot move into a position where they will be ejected from the container when it is upset or falls to the floor, etc. To place a syringe into the container, as stated, it is pushed through the flexible element 70 whereby the opposing teeth 78 tend to part as the syringe 20 is pressed through. It should be clear that the syringe is pressed into the container, needle 22 first. A detent bump 78 may be molded onto the upper teeth portion as shown in FIG. 4 so as to keep the lid flap 74 closed by sandwiching the top cover 40 between the lid flap 74 and the detent bump 78. When the container is filled, it is incinerated or otherwise discarded.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A disposable container for enclosing at least one hypodermic syringe, the container comprising:

a sidewall, top cover and bottom wall joined integrally for enclosing a space defined thereby therewithin, the top cover providing an entranceway into the space, the entranceway configured for passing at least one hypodermic syringe axially therethrough for storage of the at least one hypodermic syringe within the container, the sidewall, top cover and bottom wall being placed such that the, at least one hypodermic syringe cannot positionally reverse within the space;

the entranceway comprising a lid flap hinged integrally with the top cover, the lid flap being positionable outwardly in an open attitude for admittance of the at least one syringe into the entranceway, and alternately positionable in a closed attitude for closure of the entranceway;

the entranceway further comprising a flexible element comprising opposing intermeshed teeth made of a flexible and resilient sheet material.

2. The container of claim 1 wherein the sidewall, top cover and bottom wall are of such material and construction as to inhibit penetration by a syringe needle.

3. The container of claim 1 wherein the flexible element is curved so as to be movable in a first direction for admitting the at least one syringe into the container, and resistant to motion in an alternate direction so as to prevent the at least one syringe from moving out of the container.

4. The container of claim 1 wherein each of the syringes has a length dimension greater than the width of the interior space and greater then the height of the interior space.

5. The combination of claim 1 wherein the entranceway is mounted adjacent to one end of the container.

6. The container of claim 1 wherein each of the intermeshed teeth is formed with a lateral curvature such that each of the teeth is more easily bent toward the interior space than away from the interior space.

* * * * *